US008461840B2

(12) United States Patent
Stemmer (10) Patent No.: US 8,461,840 B2
(45) Date of Patent: *Jun. 11, 2013

(54) MAGNETIC RESONANCE METHOD AND APPARATUS TO GENERATE AN IMAGE USING A PARALLEL ACQUISITION TECHNIQUE

(75) Inventor: Alto Stemmer, Abenberg (DE)

(73) Assignee: Siemens Aktiengesellschaft, Munich (DE)

( * ) Notice: Subject to any disclaimer, the term of this patent is extended or adjusted under 35 U.S.C. 154(b) by 472 days.

This patent is subject to a terminal disclaimer.

(21) Appl. No.: 12/729,362

(22) Filed: Mar. 23, 2010

(65) Prior Publication Data

US 2010/0237865 A1  Sep. 23, 2010

(30) Foreign Application Priority Data

Mar. 23, 2009 (DE) .......................... 10 2009 014 498

(51) Int. Cl.
*G01V 3/14* (2006.01)
*G01V 3/28* (2006.01)

(52) U.S. Cl.
USPC ............................ 324/309; 324/307; 324/318

(58) Field of Classification Search
USPC .... 324/300–322; 600/407–465; 382/128–131
See application file for complete search history.

(56) References Cited

U.S. PATENT DOCUMENTS

| 7,205,763 | B2 | 4/2007 | Porter | |
|---|---|---|---|---|
| 7,309,984 | B2 * | 12/2007 | Arunachalam et al. | 324/307 |
| 7,319,324 | B2 * | 1/2008 | Kannengießer et al. | 324/309 |
| 7,482,806 | B2 | 1/2009 | Stemmer et al. | |
| 7,511,495 | B2 * | 3/2009 | Kholmovski et al. | 324/310 |
| 2004/0222794 | A1 * | 11/2004 | Griswold et al. | 324/309 |
| 2006/0028206 | A1 | 2/2006 | Zhang et al. | |
| 2008/0021304 | A1 * | 1/2008 | Stemmer | 600/410 |
| 2008/0068016 | A1 * | 3/2008 | Gaddipati et al. | 324/318 |
| 2008/0303521 | A1 | 12/2008 | Beatty et al. | |

OTHER PUBLICATIONS

"GRAPPA-accelerated shot axis BLADE EPI for multi-shot diffusion weighted imaging" A.Stemmer and B. Kiefer, Siemens AG, Healthcare Sector, Erlangen, Germay.*

(Continued)

*Primary Examiner* — Melissa Koval
*Assistant Examiner* — Emily Chan
(74) *Attorney, Agent, or Firm* — Schiff Hardin LLP (57) ABSTRACT

In a magnetic resonance a method and apparatus to generate images by a parallel acquisition technique, a first echo train is generated after a first excitation pulse, wherein the first echo train sufficiently densely scans a segment of k-space to be scanned for an acquisition of coil calibration data. Coil calibration data are acquired by means of the first echo train after the first excitation pulse. The acquired coil calibration data are stored in a coil calibration data set. A second echo train is generated after a second excitation pulse, wherein the second echo train undersamples a segment of k-space to be scanned for an acquisition of image data. Image data are acquired by means of the second echo train after the second excitation pulse. The acquired image data are stored in an incomplete image data set. An image data set is generated by substituting data missing in the incomplete image data set due to the undersampling by means of a selected PAT reconstruction technique using the coil calibration data. The first echo train and the second echo train are generated by an identical sequence technique such that each echo train has a series of echoes, with a time interval between successive echoes of the first echo train being shorter than a time interval of the second echo train.

16 Claims, 3 Drawing Sheets

OTHER PUBLICATIONS

"Parallet Imaging Methode for Split-Blade PROPELLER DWI" D.Huo et al, Imaging research, Barrow Neurological Institute, Phoenix, AZ.*

Heid et al; Eddy Current-Nulled Diffusion Weighting; Proc. Intl. Soc. Mag. Reson. Med., vol. 8, (2000) p. 799.

Pipe; The Use of Parallel Imaging with Propeller DWI; ISMRM 2003, abstract #66.

Chuang et al.; Propeller EPI with SENSE parallel imaging using a circularly symmetric phase array RF coil; ISMRM 2004, abstract #535.

Griswold et al.; Autocalibrated Coil Sensitivity Estimation for Parallel Imaging NMR in Biomedicine vol. 19 (2006) pp. 316-324.

Stemmer et al: GRAPPA-Accelerated Short Axis BLADE EPI for Multi-Shot Diffusion Weighted Imaging: 5423; ISMRM 2009.

Porter et al Multi-Shot Diffusion-Weighted EPI With Readout Mosaic Segmentation and 2D Navigator Correction.

Skare et al: Propeller EPI in the Other Direction; Magn. Reson. In Medicine vol. 55 (23006) 1298-1307.

Griswold et al: Resolution Enhancement in Single-Shot Imaging Using Simultaneous Acquisition of Spatial Harmonics (SMASH): Magn. Reson. In Medicine 41 pp. 1236-1245.

Skare et al. Clinical Multishot DW-EPI Through Parallel Imaging With Considerations of Susceptibility, Motion, and Noise. Magn. Reson. In Medicine 57 (2007); pp. 881-899.

Skare et al. An Auto-Calibrated, Angularly Continuous, Two-Dimensional GRAPPA Kernel for Propeller Trajectories; Magn. Reson. In Medicine (2008) pp. 1457-1465.

Skare et al: Diffusion Imaging Using MinD SAP-EPI: Proc.Intl Soc. Magn. Reson Med 14 (2006).

Huo et al: Parallel Imaging Method for Split-Blade PROPELLER DWI, Proc. Intl. Soc. Mag. Reson. Med. vol. 16 (2008) p. 756.

"Auto-Calibrated Parallel Spiral Imaging," Heberlein et al, Magnetic Resonance in Medicine, vol. 55 (2006) pp. 610-625.

U.S. Appl. No. 12/729,327, filed Mar. 23, 2010.

* cited by examiner

MAGNETIC RESONANCE METHOD AND APPARATUS TO GENERATE AN IMAGE USING A PARALLEL ACQUISITION TECHNIQUE

BACKGROUND OF THE INVENTION

1. Field of the Invention

The present invention concerns a method, a magnetic resonance apparatus and a computer program to generate images by means of a parallel acquisition technique.

2. Description of the Prior Art

Parallel acquisition techniques (PAT) enable the spatial frequency space (known as k-space) to be undersampled during a data acquisition (a measurement) in magnetic resonance tomography (MRT), i.e. to fall below the density of the measured data points or data lines that is required according to the Nyquist theorem and to approximately calculate the missing data points (most often whole data lines) during the image reconstruction or to directly suppress the aliasing artifacts resulting from the undersampling in the associated image space. The measurement time that must be applied to acquire the raw data can thus be markedly reduced. Furthermore, typical artifacts that occur given special applications or sequence techniques can be reduced drastically in part with the aid of the parallel acquisition techniques. The requirement in order to be able to apply parallel acquisition techniques is multiple acquisition coils and the knowledge of the spatial sensitivities of the acquisition coils used in the acquisition of the raw data; this is also called a knowledge of the coil sensitivities. The coil sensitivities can be calculated approximately from what are known as coil calibration data. The coil calibration data are normally additionally measured. The spatial information of the measurement data that is missing due to the undersampling is then compensated. with the aid of the coil calibration data or with the use of the coil sensitivities of the acquisition coils that are calculated from the coil calibration data. The missing data points are thereby either substituted with the use of the coil calibration data (or with the use of the coil sensitivities of the acquisition coils that are calculated from the coil calibration data) and the measured data points (measurement data), or the aliasing artifacts resulting from the undersampling are directly suppressed in image space with the use of the coil sensitivities. In both cases this is called a PAT reconstruction.

The coil sensitivities of the acquisition coils depend on, among other things, the orientation of the acquisition coils on the examination subject (for example a patient) and the respective load in the field, thus on properties of the examination subject at the location of the acquisition coil. The coil sensitivities therefore must be redetermined at least for every examination subject. The sensitivity of the acquisition coils can also be affected during a measurement by movements (in particular macroscopic movements) of the examination subject, for example breathing movements or other movements of a patient. The coil calibration data are therefore ideally reacquired for every measurement and in close temporal proximity to the measurement data.

Different methods to measure the coil calibration data or, respectively, to determine the coil sensitivities are described in the article by M. Griswold et al., "Autocalibrated coil sensitivity estimation for parallel imaging", M. R Biomed. 2006; 19: 316-324, for example.

However, the known methods to determine coil calibration data are not suitable for every sequence technique for the data acquisition and/or are undesirably time-consuming.

SUMMARY OF THE INVENTION

An object of the invention is to provide a method, a magnetic resonance apparatus and a computer-readable medium that enable a movement-insensitive and fast acquisition of coil calibration data for parallel acquisition techniques (PAT).

A method according to the invention to generate images by means of parallel acquisition technique includes the steps of generating a first echo train after a first excitation pulse, wherein the first echo train sufficiently densely scans a segment of k-space to be scanned for an acquisition of coil calibration data, acquiring coil calibration data by means of the first echo train after the first excitation pulse, storing the acquired coil calibration data in a coil calibration data set, generating a second echo train after a second excitation pulse, wherein the second echo train undersamples a segment of k-space to be scanned for an acquisition of image data, acquiring image data by means of the second echo train after the second excitation pulse, storing the acquired image data in an incomplete image data set, and generating an image data set by substituting data missing in the incomplete image data set due to the undersampling by means of by means of a selected PAT reconstruction technique using the coil calibration data, wherein the first echo train and the second echo train are generated by an identical sequence technique such that each echo train has a series of echoes, with a time interval between successive echoes of the first echo train being shorter than a time interval between successive echoes of the second echo train.

The invention is based on the following insights.

The autocalibration technique is a known method to determine coil calibration data that is used especially frequently given changing measurement conditions. In this a portion of k-space (for the most part the inner, central region) is scanned completely (also referred to as "densely") corresponding to the aforementioned Nyquist theorem while the remainder of k-space (corresponding for the most part to the peripheral region) is undersampled. The coil calibration data that are required for substitution of the undersampled regions are determined directly from the completely scanned region. The corresponding coil calibration data are thus determined directly during each measurement. An additional advantage of the autocalibration technique is that the densely scanned regions require no substitution, and therefore the signal-to-noise ratio (SNR) in the acquired data is improved relative to completely undersampled data.

However, the autocalibration technique is not suitable for all sequence techniques, in particular not for the echoplanar sequences (EPI sequences). For example, if this autocalibration technique is used in a single shot echoplanar sequence (single shot EPI), the coil calibration data and also the desired measurement data (most often image data) are thus acquired in a single echo train. This is possible in that the moment of the phase coding gradients (also designated as the "blip") that is switched between the acquisition of two adjacent lines varies during the echo train. For example, the moment of the phase coding gradients in the undersampled region (for example between two peripheral lines that are acquired at the beginning and at the end of the echo train) is greater by a factor of A than between two lines in the densely scanned region (for example between two central lines). A is thereby what is known as the acceleration factor. This variation in the speed with which k-space is traversed along the phase coding direction during the echo train leads to smearing artifacts that make the quality of the acquired data unsatisfactory. Therefore the autocalibration technique is not used for these sequence techniques (such as single shot EPI) in spite of its speed and movement insensitivity.

Another known method that is used in connection with EPI is the acquisition of the coil calibration data separate from the additional desired measurement data after one or more separate excitation pulses, for example in the course of a "prescan".

If the coil calibration data are thereby read out in a "prescan" after a single excitation, the phase coding gradient between the two adjacent lines of an EPI echo train that is used to acquire the image data has A times the moment of the phase coding gradient between two lines of an echo train that is used to acquire the coil calibration data. Accordingly, the speed along the phase coding direction during an imaging echo train is greater by a factor of A than during an echo train to acquire the coil calibration data. In echo planar imaging, the speed with which k-space is traversed along the phase encoding direction coincides with distortion or smearing artifacts. The different speed therefore leads to different distortions between the acquired image data and the coil sensitivities that can be determined from the coil calibration data. The different distortions can have negative effects on the PAT reconstruction. Furthermore, the $T_2^*$ decay between the acquisition of two adjacent measured lines of the image data here is proportional to $e^{-ES/T_2*}$, while the $T_2^*$ decay between the acquisition of corresponding lines in the coil calibration data set is proportional to $e^{-A \cdot ES/T_2*}$. ES is thereby the temporal echo spacing (ES), thus the time between successive echoes of the echo train. This also negatively affects the PAT reconstruction.

These two cited problems in the "prescan" method could be solved if the "prescans" are segmented, thus measured after multiple separate excitations. The coil calibration data are thereby acquired segmented using A echo trains. The moment of the phase coding gradient between two adjacent lines of the A echo trains to acquire the coil calibration data and the moment of the phase coding gradient of the imaging echo train are then equal. The speed along the phase coding direction and the $T_2^*$ decay between adjacent measured lines is therefore also equal. A phase coding prephasing gradient at the beginning of the A echo trains to acquire the coil calibration data is thereby respectively chosen so that the data of the A echo cycles together densely scan k-space. However, this segmented method again has as a disadvantage relative to the acquisition of the coil calibration data after a single excitation that more time is required for the acquisition of the coil calibration data (A echo trains instead of a single echo train), and the sensitivity of the measurement relative to movements (for example of the patient) and other physiological effects (such as flow) is increased by the segmentation.

Which method to use to determine the coil calibration data has previously depended on many factors, among other things on the PAT reconstruction technique that is used, for example GRAPPA ("generalized autocalibrating partially parallel acquisitions"), SMASH ("simultaneous acquisition of spatial harmonics") or SENSE ("SENSitivity Encoding") and/or the acceleration factor A.

In both cases, however, the time interval between the acquisition of the coil calibration data and the acquisition of the image data or desired measurement data, is at least a repetition time TR of the sequence that is used. This repetition time TR is up to multiple seconds, for example given diffusion-weighted imaging. This time interval is not negligible compared to the time constants associated with physiological movement of the examination organ (due to breathing, heart beat or peristaltic) and such can lead to inconsistencies between the acquired coil calibration data and the image data acquired with delay. These inconsistencies in turn negatively affect the quality of the parallel image reconstruction, for example in that they lead to an incomplete suppression of the aliasing artifacts resulting from the undersampling or to a degradation of the SNR.

This applies all the more in measurements in which an anatomical slice is measured repeatedly, for example with the goal of improving the SNR. However, this is the rule in diffusion-weighted imaging, for example, wherein each slice is usually measured repeatedly, not only for SNR improvement but also possibly with different alignment and/or amplitude of an applied diffusion gradient. For effectiveness, particularly with regard to the necessary acquisition time, in diffusion-weighted imaging the coil calibration data nevertheless have conventionally been most often acquired only once per slice and thereby normally with deactivated diffusion gradients. The time interval between acquisition of the coil calibration data and the image data thereby even amounts to multiple TR intervals.

With the method according to the invention the first echo train and the second echo train are generated by an identical sequence technique, such that each echo train includes a series of echoes, wherein the time interval between successive echoes of the first echo train is shorter than the time interval between successive echoes of the second echo train. The total measurement duration of the two acquisitions is reduced by the shortening the echo spacing of the first echo train. Moreover, the speed along the phase coding direction in the two echo trains is simultaneously matched to one another, and therefore the distortion artifacts in the respective data that have been mentioned above are likewise matched. The subsequent substitution via a PAT reconstruction technique is thus no longer negatively affected by inconsistencies in the respective distortions. The T2* decay between the acquisition of corresponding k-space lines in the coil calibration data set and in the image data set is likewise adapted, so the aforementioned disadvantages are likewise avoided without the measurement duration having to be extended and the sensitivity to movement and flow having to be increased (as in the prior art).

The time interval between successive echoes of the first echo train is particularly advantageously shortened by a factor of A relative to the time interval between successive echoes of the second echo train, and at the same time the spacing between lines scanned by means of the first echo train in the segment of k-space densely scanned for the acquisition of the coil calibration data is shortened by the same factor A relative to the spacing of lines scanned by means of the second echo train in the segment of k-space undersampled for the acquisition of image data. In this way the adaptation of the speed along the phase coding directions and the adaptation of the "T2* decay are optimized.

The first echo train and the second echo train are advantageously generated using a sequence technique for echoplanar imaging (EPI). Echoplanar imaging is characterized by a particularly fast data acquisition and thus shortens the acquisition times for the respective data. However, it is also possible to use a sequence technique for turbo spin echo (TSE) imaging, for example.

In an embodiment, the first excitation pulse and the second excitation pulse are one and the same excitation pulse. The time interval between the acquisition of the coil calibration data and the image data can thus be kept small via the acquisition of the coil calibration data and the image data after a common excitation pulse, in particular smaller than a repetition time TR of the data measurement. Depending on the sequence technique and the hardware that are used, in particular depending on the gradient system, the time interval between the acquisition of the coil calibration data and the acquisition of the image data can be shortened to a few tenths of a millisecond, so it is below the temporal time constants associated with the typical macroscopic movements of examination subjects (for example breathing or heart beat of a patient). A robust parallel image reconstruction is therefore possible under typical macroscopic movements of the examination subject without the cited disadvantages of the known autocalibration techniques given special sequence techniques (such as echoplanar sequences).

In another embodiment of the method the coil calibration data set and the imaging data are acquired in segmented fashion. A series of excitation pulses is radiated into the examination subject and, after each excitation pulse, one segment of the k-space acquired for the acquisition of the coil calibration data or one segment of the k-space to be acquired for the acquisition of image data is acquired. The amount of data of the two acquired data sets (consisting of the superimposed k-space segments) can be increased via such a segmented acquisition with more excitation pulses (for example given an unchanged echo train length), and thus for example the resolution of the calculated images can be improved. Furthermore, given such a segmented acquisition of coil calibration data and image data the speed with which k-space is traversed along the phase coding direction during the echo train can be increased, and therefore distortion artifacts can be reduced.

In the embodiment just cited the first echo train and second echo train are generated by an echoplanar imaging (EPI) sequence, wherein the different segments are rotated relative to one another. A known sequence technique for this purpose is, for example, known as the PROPELLER EPI. A PROPELLER method in connection with parallel acquisition technique is described in U.S. Pat. No. 7,482,806. However, due to the variable speeds occurring there in the phase coding direction, this is not suitable for EPI techniques for the aforementioned reasons.

In PROPELLER methods the parallel reconstruction ensues individually for each segment (also called "blade") before a superposition of the blades. By applying a method according to the invention with a PROPELLER EPI technique, matching coil calibration data are acquired for each segment of k-space that is scanned, and therefore for each orientation of the segment. The time that is required for acquisition of the coil calibration data can extend the echo time, in EPI sequences the echo time is the time interval between excitation pulse and acquisition of the central k-space line. However, this extension is usually small, for example, in a diffusion weighted spin-echo EPI sequence the time between excitation pulse and first inversion pulse can normally not fully be used, for example due to a desired symmetry of the diffusion module and a minimum number of lines that must be acquired before the central k-space line.

Therefore, in spite of acquisition of matching coil calibration data for every scanned segment the method is particularly time-efficient since coil calibration data and image data can in fact be acquired by means of two echo trains, but after a common excitation pulse. In spite of the generation of a first echo train and a second echo train after the common excitation pulse the acquisition time for one blade does not necessarily need to be extended since, for example otherwise unused fill times of the sequence that occur in some sequence techniques are used for the acquisition of the first echo train. Depending on the sequence technique that is used, however, under the circumstances an extension of the time between two excitation pulses is necessary. However, the extension of the total measurement time that results in this case is normally negligible relative to an extension of the total measurement time as it arises given separate acquisition of coil calibration data and image data.

In another embodiment, artifacts in the incomplete image data set and/or in an image data set obtained from the incomplete image data set (by means of the parallel reconstruction technique) are corrected on the basis of the coil calibration data set. Since the coil calibration data of the coil calibration data set have been acquired by means of an echo train completely scanning a segment of k-space, these data can be used for example to compare results of the reconstruction and/or for an averaging of data present once in this way in the coil calibration data set and once in the (possibly already substituted) incomplete image data set, so the SNR can be further increased, for example.

A magnetic resonance apparatus according to the invention has multiple acquisition coils to acquire radio-frequency signals and a control computer that is fashioned to implement the method described above.

A non-transitory computer-readable medium according to the invention is encoded with programming instructions to implement a method described above in a computer that operates a magnetic resonance apparatus when the programming instructions executed by the computer.

DESCRIPTION OF THE PREFERRED EMBODIMENTS

Figure 1:
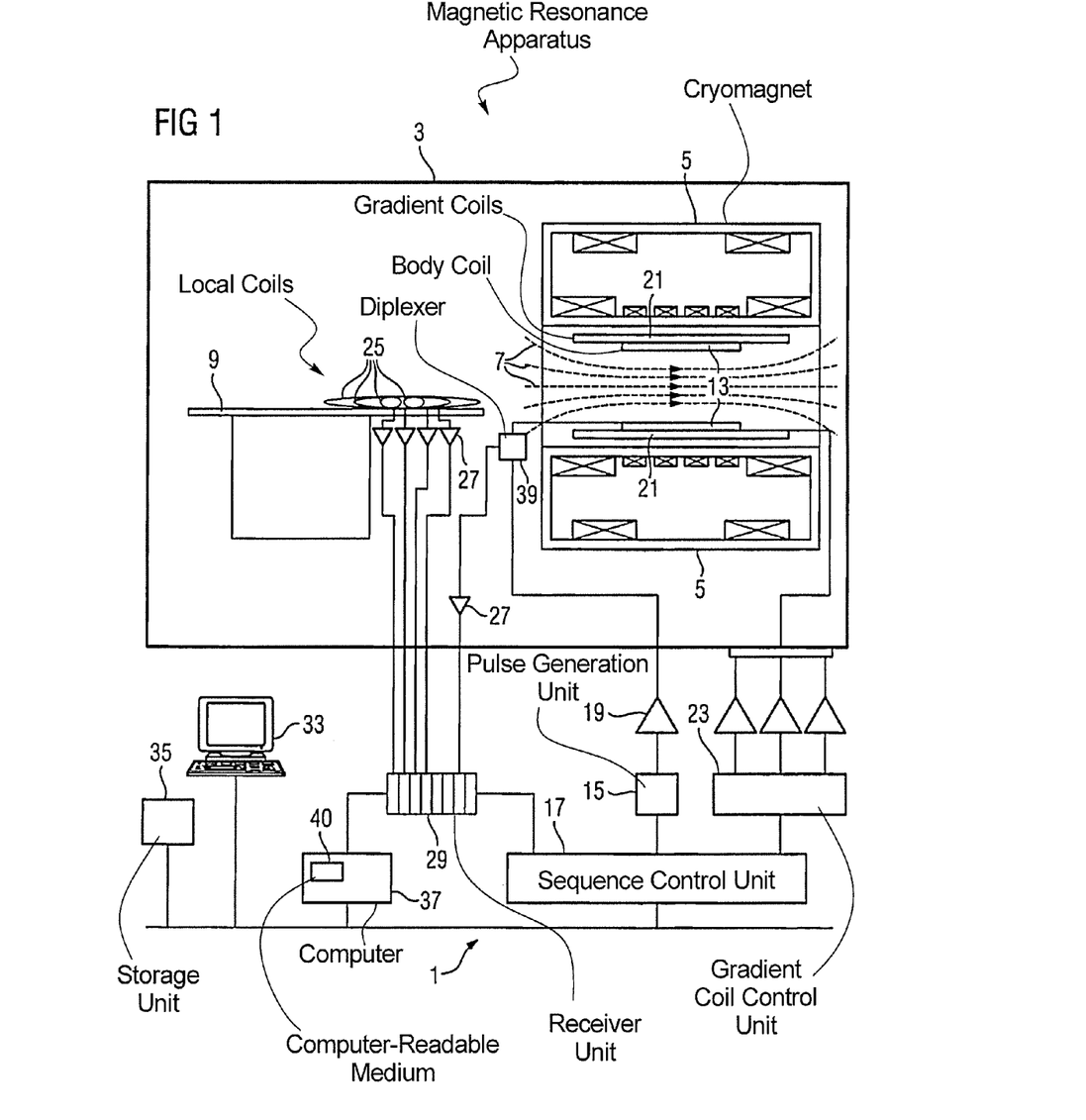
FIG. 1 schematically illustrates a magnetic resonance apparatus operable in accordance with the invention.

FIG. 1 schematically shows the basic components of a magnetic resonance apparatus 1. In order to examine a body by means of magnetic resonance imaging, various magnetic fields, that are matched to one another as precisely as possible with regard to their temporal and spatial characteristics, are radiated into the body of a subject.

A strong magnet (typically a cryomagnet 5 with a tunnel-shaped opening) arranged in a radio-frequency-shielded measurement chamber 3 generates a static, strong basic magnetic field 7 that is typically 0.2 Tesla to 7 Tesla or more. An examination subject (for example a patient; not shown here) to be examined is supported on a patient bed 9 and is positioned in the homogeneous region of the basic magnetic field 7.

Excitation of nuclear spins in the examination subject ensues by means of radio-frequency excitation pulses that are radiated with at least one radio-frequency antenna, for example a radio-frequency antenna shown here as a body coil 13. The radio-frequency excitation pulses are generated by a pulse generation unit 17. After amplification by a radio-frequency amplifier 19, they are relayed to the at least one radio-frequency antenna. The radio-frequency system shown here is only schematically indicated. Typically more than one pulse generation unit 15, more than one radio-frequency amplifier 19 and multiple radio-frequency antennas are used in a magnetic resonance apparatus 1.

Furthermore, the magnetic resonance apparatus 1 has gradient coils 21 with which magnetic gradient fields are radiated in a measurement (data acquisition) for, among other things, selective slice excitation and spatial coding.

The gradient coils 21 are controlled by a gradient coil control unit 23 that, like the pulse generation unit 15, is connected with the pulse sequence control unit 17.

The signals emitted by the excited nuclear spins are received by the body coil 13 and/or local acquisition coils 25, amplified by associated radio-frequency preamplifiers 27 and further processed and digitized by a receiver unit 29.

In the case of a coil that can be operated both in transmission mode and in acquisition mode (for example the body coil 13), the correct signal relaying is regulated by an upstream transmission/reception diplexer 39.

A computer 37 that is connected with the magnetic resonance apparatus processes the measurement data. In particular, the computer 37 implements a PAT reconstruction of received measurement data (for example), wherein the computer 37 is connected with a memory unit 35 such that the computer 37 can store results of the PAT reconstruction as well as intermediate results of the processing of the measurement data, for instance (incomplete) image data sets or coil calibration data sets, in the memory unit 35 and also retrieve them again. Furthermore, the computer 37 can generate images from the measurement data (possibly under additional processing steps, for example corrections) that can be presented to a user via an operator console 33 or be stored in the memory unit 35. The computer 37 furthermore controls the individual system components, in particular during the acquisition of the measurement data. The computer 37 is fashioned so that the method according to the invention can be implemented with it. For example, a computer-readable medium 40 according to the invention is installed on the computer 37 such that programming instructions encoded therein can be executed, the programming instructions encoded in the computer program 40 thus implement a method according to the invention in the computer 37 when it is executed in the computer.

The shown units (in particular the computer 37 and the memory unit 35) are not necessarily to be understood as a physical unit; rather, they can also be composed of multiple sub-units that are possibly arranged physically separately from one another.

Figure 2:
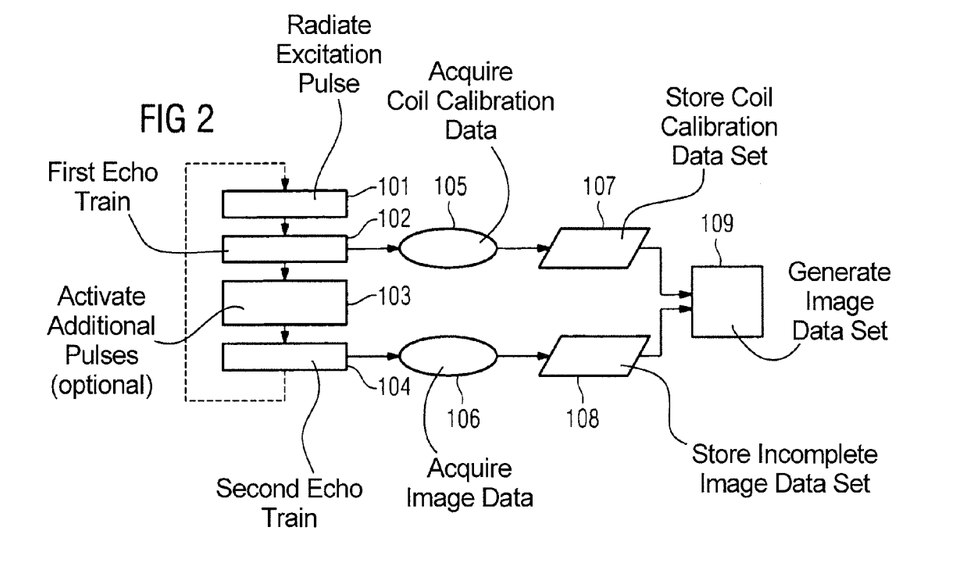
FIG. 2 is a flowchart of an embodiment of the method according to the invention.

FIG. 2 shows a flowchart of an embodiment of the method according to the invention for the generation of image data sets by means of a parallel acquisition technique. An excitation pulse is radiated into an examination subject in a first Step 101.

After the excitation pulse a first echo train is generated in a further Step 102. The first echo train hereby scans a segment of k-space to be densely scanned for an acquisition of coil calibration data. The signals generated in the examination subject by the first echo train are acquired as coil calibration data 105 and stored in a coil calibration data set 107.

In a further Step 104, a second echo train is likewise generated after the excitation pulse from Step 101. A segment of k-space to be scanned for an acquisition of image data is hereby undersampled by the second echo train. The signals generated in the examination subject by the second echo train are acquired as image data 106 and stored in an incomplete image data set 108.

Additional pulses or special gradient fields to prepare specific signals can advantageously be switched (activated) between the first echo train and the second echo train in Step 103. For example, at least one inversion pulse can be switched to refocus phases of different spins in the examination subject. Furthermore, in Step 103 it is possible to switch at least one diffusion gradient between the first echo train and the second echo train. For example, diffusion-weighted image data can thus be acquired.

In a last Step 109, an image data set is obtained from the incomplete image data set in that data missing in the incomplete image data set are substituted using the coil calibration data set by means of a selected PAT reconstruction technique. Possible PAT reconstruction techniques are, for example, the aforementioned GRAPPA, SENSE or SMASH. The possible workflow of such a reconstruction is explained more precisely later in connection with FIG. 6.

The image data set so obtained can be additionally processed, stored and/or displayed, as is generally indicated with regard to FIG. 1.

Steps 101 through 104 are possibly repeated for multiple segments of k-space, as is indicated by the dashed arrow in FIG. 2. A series of excitation pulses is thus radiated into the examination subject, wherein coil calibration data sets 107 and incomplete image data sets 108 are acquired after each excitation pulse (thus for each segment) from which in Step 109 at least one image data set is generated by means of the selected PAT reconstruction technique. If both coil calibration data and image data are acquired by means of a first echo train and a second echo train after each excitation pulse, the results of the PAT reconstruction are particularly reliable since the respective coil calibration data have respectively been obtained in close temporal proximity to the corresponding image data. Movement sensitivity of the method is thus reduced. Under the circumstances it is already sufficient if coil calibration data and image data are only acquired after one (for example the first) excitation pulse in the manner described above, and only image data are acquired after the remaining excitation pulses of the series. Under the circumstances this increases the time efficiency but degrades the movement insensitivity of the method.

Figure 3:
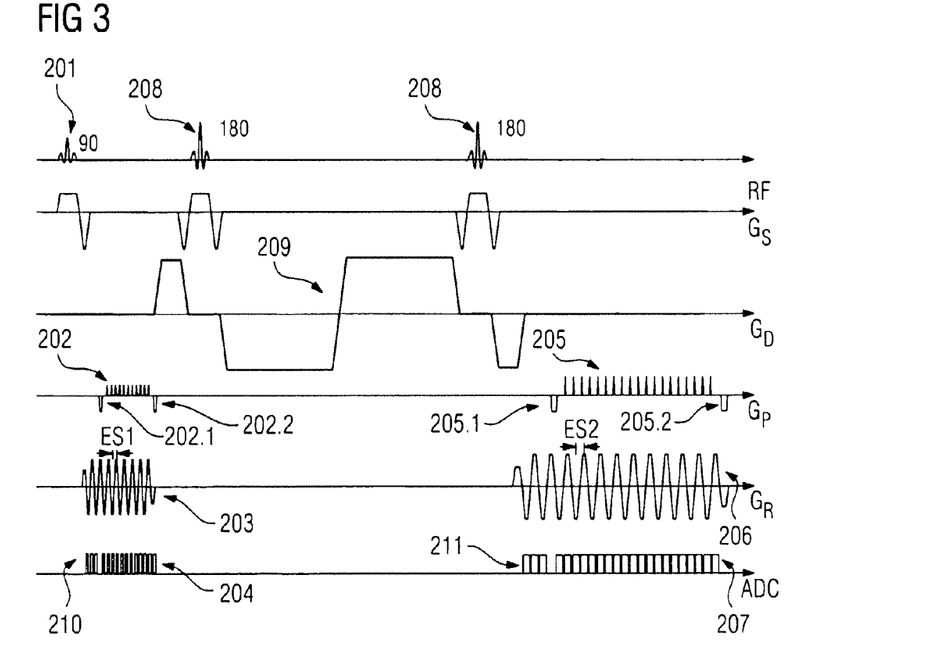
FIG. 3 is a sequence diagram with which the method according to the invention can be implemented.

FIG. 3 shows a schematic sequence diagram in the example of a basic sequence suitable for echoplanar imaging (EPI) with which a method according to the invention can be advantageously implemented. The time sequence of radio-frequency pulses (time line RF), exemplary slice-selection gradients (time line Gs), possible diffusion gradients (time line Go) to be switched, exemplary phase coding gradients (time line Gp), possible readout gradients (time line GR) and the signal acquisition (time line ADC) is set with the aforementioned items in relation to one another in a conventional manner.

After an excitation pulse 201—for example a 90° pulse 90—a first echo train 204 (signal not explicitly shown) is generated and acquired by means of a series of first readout gradients 203 and by means of a series of first phase coding gradients 202, and after the same excitation pulse 201 a second echo train 207 (signal not explicitly shown) is generated and acquired by means of a series of second readout gradients 206 and by means of a series of second phase coding gradients 205. Less time-efficient but also conceivable is a respective generation of the first echo train and second echo train in separate sequences (not shown) after a separate excitation pulse that respectively acts on the same slice in the examination subject. Such a sequence to generate a first echo train can hereby be designed so that, for example, possible navigator echoes and subsequently the first echo train are generated after the excitation pulse. Navigator echoes are additional echoes that are generated and acquired for the purpose of artifact correction and are explained in more detail later. Here as well inversion pulses and/or diffusion gradients can possibly be additionally switched between the excitation pulse and the generation of the first echo train. In this case the navigator echoes can be generated chronologically before or after the possibly switched inversion pulses and diffusion gradients. The generation of the navigator echoes and the first echo train can hereby otherwise ensue analogous to the sequence shown in FIG. 3. Such a sequence to generate a second echo train after a separate excitation pulse can analogously be designed so that, for example, possible navigator echoes and subsequently the second echo train are generated after the excitation pulse. Here as well inversion pulses and/or diffusion gradients can possibly be additionally switched between the excitation pulse and the generation of the second echo train. In this case the navigator echoes can be generated chronologically before or after the possibly switched inversion pulses and diffusion gradients. The generation of the navigator echoes and the second echo train can hereby otherwise ensue analogous to the sequence shown in FIG. 3.

The data acquired during the readout can in both cases (separate excitation pulses or a common excitation pulse) be respectively stored as in corresponding data sets as described above, wherein coil calibration data are obtained from the first echo train and incomplete image data are obtained from the second echo train. The series of first and second phase encoding gradients 202, 205 is respectively represented as a series of what are known as "blips" in FIG. 3.

The first echo train 204 thereby sufficiently scans k-space while the second echo train 207 undersamples k-space. A sufficiently dense scan can also be an oversampling according to the Nyquist theorem, meaning that more data points than are necessary according to the Nyquist theorem can also be measured.

At least one inversion pulse 208—for example a 180 degree pulse 180—can be switched temporally between the first echo train 204 and second echo train 207 and the second echo train can be acquired in a time window in which the peak of a spin echo also lies, which spin echo is generated by the excitation pulse 201 and the at least one inversion pulse 208. Artifacts in the images—for example as a result of signal loss in regions with varying magnetic susceptibility or as a result of inhomogeneities of the magnetic field—can thereby be reduced, in particular when the central k-space lines of the incomplete image data set are acquired in immediate proximity to the spin echo.

Furthermore, at least one diffusion gradient 209 can be switched between the first echo train 204 and the second echo train 207 in order to acquire diffusion-weighted image data by means of the second echo train, which in this case is generated chronologically after the diffusion gradient 209. For the signal quality it is again advantageous to switch one or more inversion pulses 208 between the diffusion gradients 209. If the coil calibration data 204 are obtained in this way before the diffusion gradients 209, they are not subject to the diffusion weighting generated by the diffusion gradients 209.

A time interval between acquisition of the coil calibration data and the image data—thus a time interval between the first echo train and second echo train—is hereby on the order of the a few tenths of a millisecond. A current value of the time interval thereby depends on the desired maximum diffusion weighting of the acquired images that is normally specified as a b-value. The time that is required in order to achieve a specified maximum diffusion weighting in turn depends on the gradient system of the magnetic resonance apparatus, in particular the maximum gradient amplitude. The maximum gradient amplitude of clinical MR tomographs is presently above 10 mT/m, and the maximum desired diffusion weighting is normally around b=1000 s/mm$^2$. Under these conditions, the time interval of the two echo trains is normally markedly below 100 ms. The lower limit of the time interval between the two echo trains given a small maximum diffusion weighting (b~50 s/mm$^2$) or without diffusion gradient is limited by the duration of the first echo train and the duration of the inversion pulse. It can be specified with 5 ms. The time interval thus lies in a range between 5 ms and 100 ms and is therefore markedly shorter than the typical time constants of the human cardiac cycle (~one second) and human breathing (3-10 seconds). A particularly low movement sensitivity of the sequence is thus provided.

Furthermore, it is advantageous if additional navigator echoes 210 are generated with the first echo train and additional navigator echoes 211 are generated with the second echo train, which navigator echoes 210, 211 are acquired under readout gradients of the series 203 or, respectively, 206 and are respectively stored as navigator data. During the acquisition of the navigator data from the navigator echoes 210 or, respectively, 211 the accumulated gradient moment in the phase coding direction is equal to zero. This can be achieved, for example, by acquiring the navigator data at the beginning of the respective echo train and by activating each phase encoding prephasing gradient 202.1 and 205.1 after the acquisition of the respective navigator data, and with no phase encoding gradient 202 or 205 being activated between the navigator echoes.

The acquired navigator data can be used to correct phase differences between even and odd echoes of the respective associated echo train 204, 207. Such phase differences can, for example, arise due to non-optimally balanced gradient moments that, without correction, lead to artifacts, for instance to what are known as Nyquist ghosts or N/2 ghosts.

In the example shown in FIG. 3, the three first echoes are respectively generated as navigator echoes 210, 211, acquired under the respective first readout gradients of the series 203, 206 and respectively stored as sets of navigator data. The respective fourth echo is not acquired since a phase coding prephasing gradient 202.1, 205.1 is switched parallel to this. The respective following echoes form the first or, respectively, second echo train in the sense of the method according to the invention. After the phase coding prephasing gradient 202.1, 205.1, and after a series of phase coding gradients 202, 205, a phase coding rephasing gradient 202.2, 205.2 is advantageously respectively switched having a moment that is set such that the accumulated moment of the phase coding prephasing gradient 202.1 and 205.1, all phase coding gradients of the series 202 and 205, and the phase coding rephasing gradient 202.2 and 202.5 are equal to zero.

An echo spacing ES1—thus a time interval between echoes and therefore the time between the acquisition of immediately successive phase coding lines—of the first echo train 202 is thereby shorter than a time interval (echo spacing) ES2 between successive echoes of the second echo train. In particular ES2=A*ES1 applies, for example, wherein A is the acceleration factor. It is particularly advantageous to simultaneously select the moment of a phase coding gradient of the second series of phase coding gradients 205 equal to A-times the moment of a phase coding gradient of the series 202. This results in a spacing d1 in k-space (see also FIG. 4) of two k-space lines acquired during successive echoes of the first echo train being shorter by the acceleration factor A than a spacing d2 in k-space (see FIG. 4) of two k-space lines acquired during successive echoes of the second echo train, such that it additionally applies that d2=A*d1.

The adaptation of the speed with which k-space is traversed along the phase encoding direction and the adaptation of the T2* decay are optimized in this way. However, it is also possible for $ES2=A'*ES1$ and $d2=A*d1$, with $1<A'<A$ to apply for the echo spacing and the line spacing.

This means that the echo spacing ES1 in the first echo train is shortened relative to the echo spacing ES2 in the second echo train by less than the acceleration factor A.

Figure 4:
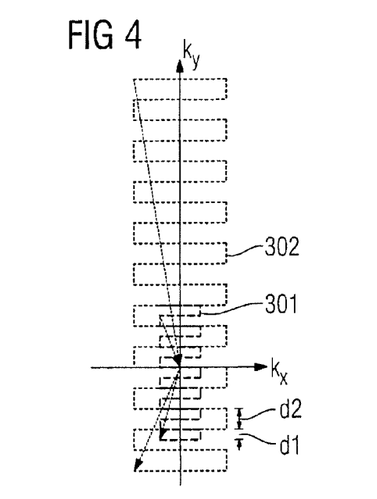
FIGS. 4 and 5 show examples of trajectories in k-space that are scanned in the method according to the invention.
Figure 5:
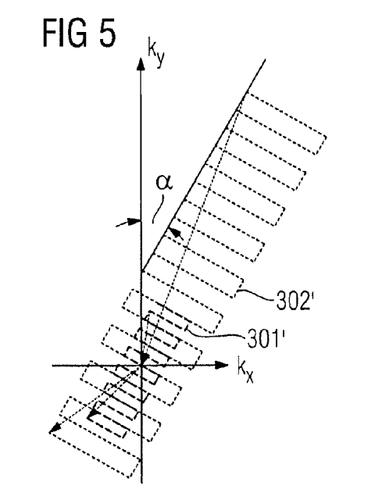

Possible k-space trajectories resulting from first and second echo trains generated in such a manner are shown as examples in FIGS. 4 and 5. The dashed k-space trajectory 301, 301' corresponds to the first echo train and the dotted k-space trajectory 302, 302' corresponds to the second echo train, wherein an acceleration factor A=2 was set in the depictions of FIGS. 4 and 5. The distance between two adjacent lines that are scanned during the first echo train is thus smaller by half than the distance between two adjacent lines that are scanned during the second echo train. As already mentioned above, the echo spacing of the first echo train is thereby ideally shorter by the aforementioned acceleration factor A than the echo spacing of the second echo train. For this purpose, it is accepted that the distance that the k-space trajectory 301 traverses along the readout direction (for example kx in FIG. 4) during an echo is shorter than the distance that the k-space trajectory 302 traverses along the readout direction (for example kx in FIG. 4) during an echo.

The segment of k-space that is scanned by the second echo train advantageously comprises the segment of k-space that is scanned by the first echo train. In particular if specific k-space points are scanned in this way with both the first and the second echo train, and therefore are stored in both the coil calibration data set and the incomplete image data set, artifacts in the incomplete image data set and/or in an image data set obtained from the incomplete image data set can additionally be advantageously corrected on the basis of the coil calibration data set.

FIG. 5 differs from FIG. 4 in that the k-space trajectories 301' and 302' were rotated by an angle a in k-space relative to the k-space trajectories 301 an 302 from FIG. 4, as is typical in PROPELLER sequences, for example. A different segment of k-space than in FIG. 4 is thus scanned here.

Such k-space trajectories 301, 301', 302, 302' are also designed as "single propeller blades" ("blades") in connection with PROPELLER sequence due to their shape. The scanning of different propeller blades hereby occurs depending on an excitation pulse, as was already described with regard to FIG. 2, for example. For the acquisition of the complete data (thus all desired segments of k-space) the basic sequence depicted in FIG. 3 is thereby repeated for every segment, wherein the direction of the propeller blade (and therefore the direction of the applied phase coding gradients and readout gradients) varies. For the acquisition of a complete PROPELLER data set, the direction of the propeller blade is hereby successively rotated around the k-space center until all segments together cover a circular region around the k-space center.

Even if a PROPELLER sequence is not used, the basic sequence shown in FIG. 3 can be repeated in the described manner, wherein for example the moment and/or the direction of possibly applied diffusion gradients is varied in order to obtain different diffusion-weighted image data.

Diffusion-weighted (DW) imaging refers to the use of magnetic resonance imaging techniques that exhibit diffusion properties of the examined tissue. Diffusion is the Brownian movement of molecules in a medium. In such techniques the diffusion of water molecules upon the application of a gradient field leads to a phase dispersion of the transversal magnetization that leads to an attenuation of the acquired signal. The magnitude of the signal attenuation depends on the duration and amplitude of the gradient field as well as on the type of tissue and its microstructure.

The strong gradient fields that are used in diffusion-weighted imaging make the techniques extremely sensitive to macroscopic movements (for example patient movements) during the diffusion preparation (thus during the switching of diffusion gradients). The radio-frequency pulse pulses and gradients of the basic sequence that primarily serve for the diffusion preparation of the transversal magnetization are frequently also designated as a diffusion module, and the remaining gradients and possible RF pulses that serve primarily to generate an echo train are designated as a readout module. Particularly fast image acquisition techniques can be used in order to avoid artifacts due to macroscopic movements during the diffusion preparation. Among such particularly fast acquisition techniques are, for example, single shot EPI techniques that allow a complete image to be acquired after a single excitation pulse and diffusion module. Artifacts that occur often given typical single shot EPI techniques, for example distortions at susceptibility boundaries, can be avoided or strongly reduced by the method described above since the speed with which k-space is traversed along the phase encoding direction is increased by the undersampling during the second echo train. At the same time, as already described above a movement sensitivity of the method is not increased as in PAT methods usually used in conjunction with EPI sequences. Therefore the method according to the invention is in particular suited for diffusion imaging with EPI techniques.

In tests a marked improvement of the image quality of diffusion-weighted images of the brain of a test subject that were acquired with a short-axis PROPELLER EPI sequence relative to a conventional short-axis PROPELLER EPI sequence without measures according to the invention could be demonstrated via use of the method according to the invention. The following parameters were thereby selected, for example:

Acceleration factor A=2; matrix size: 256; FOV ("field of view"): 230 mm; TR=3000 ms; TE=73 ms; slice thickness: 4 mm; diffusion weighting, isotropic b=1000 s/mm$^2$; readout length 64; 16 PROPELLER blades per image; echo train length: 88 ms; echo spacing for the imaging echo train: ES2=500 µs; echo spacing for the echo train with which coil calibration data were acquired: ES1=250 µs.

In DW imaging with PROPELLER acquisition techniques it is conceivable that coil calibration data are respectively acquired only once for each orientation of the propeller blades (thus the segments), for example given the least diffusion gradients and that these coil calibration data are used for the substitution of incomplete image data which were acquired with the same orientation but different diffusion gradients. Although the time efficiency of the method is thereby normally additionally increased, losses in the movement insensitivity must be accepted.

As an alternative to EPI techniques, the first echo train and second echo train can also be generated otherwise, analogous to a sequence technique for turbo spin echo (TSE) imaging.

Figure 6:
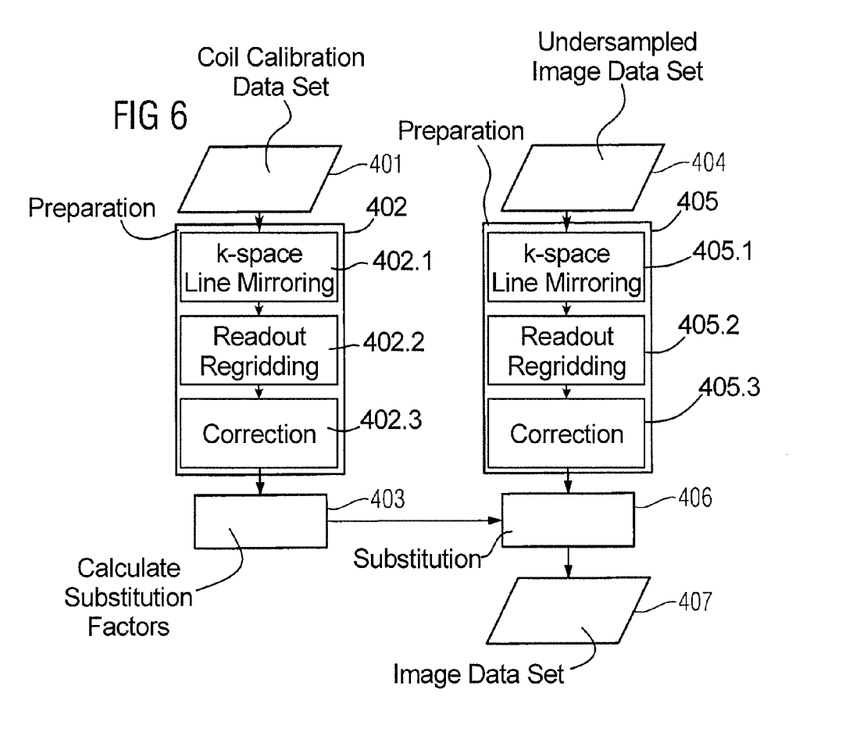
FIG. 6 is a flowchart of a basic PAT reconstruction.

A flowchart for the implementation of a principle PAT reconstruction as it can be used in Step 109 from FIG. 2 is schematically shown in FIG. 6.

A densely (or sufficiently) scanned (sampled) coil calibration data set 401—for example the coil calibration data set 107 from FIG. 2—and an undersampled (and therefore incomplete) image data set 404—for example the incomplete image data set 108 from FIG. 2—are hereby advantageously prepared first for the substitution (Steps 402 and 405).

The preparation 402 of the coil calibration data set 401 and/or the preparation 405 of the incomplete image data set 404 can include mirroring 402.1, 405.1 of every second k-space line at the origin in the readout direction if the direction of the associated k-space trajector(y/ies) alternates in successive echoes in the readout direction ($k_x$ direction in FIG. 4) as in an EPI k-space trajectory. The data are thus "aligned", so to speak, which facilitates the additional processing.

Furthermore, the preparation 402 of the coil calibration data set 401 and/or the preparation 405 of the incomplete image data set 404 can include an interpolation 402.2, 405.2 to a Cartesian grid ("readout regridding"). A varying interval in k-space between data points acquired with constant time interval, possibly due to a non-ideal readout gradient, is hereby compensated. The individual data points are accordingly arranged on a Cartesian grid, which normally drastically simplifies the further processing steps. In particular, particularly efficient algorithms such as the fast Fourier transformation can therefore be used. Such non-ideal readout gradients arise given EPI sequences, for example, if the data acquisition starts before reaching a plateau of a trapezoidal readout gradient. Such a data acquisition, also called "ramp sampling", is used to minimize the echo spacing of the EPI sequence that is thereby possible, for example. A short echo spacing in turn increases the speed with which the k-space trajectory is traversed along the phase coding direction.

If navigator data associated with the coil calibration data set 401 and/or the incomplete image data set 404 are also present, for example via an acquisition of navigator data as it can ensue in the basic sequence described with regard to FIG. 3, it is furthermore possible that the preparation 402 of the coil calibration data set 401 and/or the preparation 405 of the incomplete image data set 404 includes a correction 402.3, 405.3 of phase inconsistencies between even and odd echoes of an echo train by means of which the coil calibration data set 401 was acquired, or between even and odd echoes of an echo train by means of which the incomplete image data set 404 was acquired. The cited phase inconsistencies can be detected from the navigator data and then can be corrected for the following echoes of the echo train. For example, Nyquist ghost artifacts in images that are calculated from the coil calibration data set 401 or, respectively, the incomplete image data set 404 can thereby be avoided or, respectively, at least reduced.

The order in which the cited preparation steps 402.1, 402.2, 402.3 and 405.1, 405.2, 405.3 are shown in FIG. 6 if they are all included in the respective preparations 402 and 405 is only an example.

In a next Step 403 factors (for example) are calculated from the (possibly prepared) sufficiently scanned coil calibration data set, by means of which the data missing in the undersampled, incomplete image data set are substituted in a further Step 406.

This is explained in the following in the example of a GRAPPA PAT reconstruction.

In GRAPPA the signal $s_i(\vec{k})$ of every missing k-space point $\vec{k}$ (which is missing because it is not scanned due to the undersampling) is expressed as a linear combination of the measured (thus scanned) points adjacent to this point $\vec{k}$:

$$s_i(\vec{k}) = \sum_{j=1}^{N_C} \sum_{\vec{q} \in \Omega} n_{i,\vec{k}}(j, \vec{q}) s_j(\vec{q});$$

with $i=1, \ldots, N_C$ and $n_{i,\vec{k}}$ as linear factors (what are known as "GRAPPA weights"), wherein the first sum counts the acquisition coils (thus $N_C$ is equal to the number of participating acquisition coils of the magnetic resonance apparatus), the second sum counts all data points measured in a neighborhood $\Omega_{\vec{k}}$ of $\vec{k}$, and $s_j(\vec{q})$ represents the measured signal of the acquisition coil j at the sample point $\vec{q}$. Given Cartesian scanning, the linear factors are hereby independent of $\vec{k}=(k_x,k_y)$ and can therefore be calculated from those data of the coil calibration data set for which the $s_i(\vec{k})$ values on the left side of the above equation system are known.

In GRAPPA the factors $n_{i,\vec{k}}$ for the substitution are thus calculated in Step 403, for example via a pseudo-inversion of the above equation system. In Step 406 the data missing in the incomplete image data set are subsequently calculated by inserting the calculated factors $n_{i,\vec{k}}$ into the above equation system.

Instead of GRAPPA, another known PAT reconstruction method can also be used, for example SMASH or SENSE.

In Step 406 the undersampled (and therefore incomplete) image data set 404 is thus supplemented by means of the data calculated in Step 403 and subjected to possible additional known corrections (depending on the sequence technique used for the data acquisition) and/or processing steps in order to obtain an image data set 407. For example, if a single shot EPI sequence technique is used for the data acquisition of the incomplete image data set, a two-dimensional, discrete Fourier transformation can already be sufficient as an additional processing step in order to obtain the image data set. Additional corrections can be implemented on the basis of the coil calibration data set, for example, in that a comparison of signals of k-space points that were scanned both in the coil calibration data set 401 and in the incomplete image data set 404 is implemented, for example.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to generate magnetic resonance image data sets using a parallel acquisition technique, comprising the steps of:
   generating a first echo train after radiating a first excitation pulse into an examination subject, said first echo train sufficiently densely scanning a segment of k-space to be scanned for an acquisition of coil calibration data;
   acquiring said coil calibration data from said first echo train after said first excitation pulse;
   electronically storing the acquired coil calibration data in a coil calibration data set;
   generating a second echo train after a second excitation pulse, said second echo train undersampling a segment of k-space to be scanned for an acquisition of image data;
   acquiring said image data from said second echo train after said second excitation pulse;
   electronically storing the acquired image data in an incomplete image data set;
   generating an image data set by substituting data that are missing in the incomplete image data set due to the undersampling, using a selected parallel acquisition reconstruction technique using said coil calibration data; and
   generating said first echo train and said second echo train with an identical sequence technique such that each of said first and second echo trains to be comprised of a series of echoes, with a time interval between successive echoes of the first echo train being shorter than a time interval between successive echoes of the second echo train.

2. A method as claimed in claim 1 comprising generating said first and second echo trains with said identical sequence technique such that said interval between successive echoes of said first echo train to be shorter by a factor of A than said interval between successive echoes of said second echo train, and scanning said segment of k-space for the acquisition of said coil calibration data with an interval between k-space lines that is shorter by said factor A than an interval of k-space lines scanned by said second echo train in the segment of k-space that is undersampled for the acquisition of said image data.

3. A method as claimed in claim 1 comprising generating said first and second echo trains using an echo planar imaging sequence.

4. A method as claimed in claim 1 comprising generating said first and second echo trains with a sequence wherein said segment of k-space scanned for the acquisition of coil calibration data and said segment of k-space scanned for the acquisition of said image data each comprise an entirety of k-space.

5. A method as claimed in claim 4 comprising generating said first and second echo trains with a single shot echo planar imaging sequence.

6. A method as claimed in claim 1 comprising generating said first and second echo trains with a turbo spin echo imaging sequence.

7. A method as claimed in claim 1 comprising employing the same excitation pulse as said first excitation pulse and said second excitation pulse.

8. A method as claimed in claim 7 comprising activating at least one inversion pulse between said first echo train and said echo train.

9. A method as claimed in claim 7 comprising activating at least one diffusion gradient between said first echo train and said second echo train.

10. A method as claimed in claim 9 comprising generating said first echo train chronically before activating said at least one diffusion gradient.

11. A method as claimed in claim 7 comprising radiating a series of excitation pulses into the examination subject and scanning respectively different segments of k-space after the respective excitation pulses for the acquisition of said coil calibration data and for the acquisition of said image data.

12. A method as claimed in claim 11 comprising generating said first and second echo trains using a PROPELLER echo planar imaging sequence with said respective segments of k-space scanned for acquisition of said coil calibration data and scanned for said acquisition of said image data being scanned by rotating a PROPELLER blade.

13. A method as claimed in claim 1 comprising scanning a segment of k-space with said second echo train that contains the k-space segment that was scanned with said first echo train.

14. A method as claimed in claim 1 comprising correcting artifacts in at least one of said incomplete image data set and said image data set using said coil calibration data set.

15. A magnetic resonance apparatus to generate magnetic resonance image data sets using a parallel acquisition technique, comprising:
a magnetic resonance data acquisition units:
a control unit configured to operate said data acquisition unit to generate a first echo train after a first excitation pulse, said first echo train sufficiently densely scanning a segment of k-space to be scanned for an acquisition of coil calibration data, and to acquire said coil calibration data from said first echo train after said first excitation pulse;
a memory;
said control unit being configured to store the acquired coil calibration data in a coil calibration data set in said memory;
said control unit being configured to operate said data acquisition unit to generate a second echo train after a second excitation pulse, said second echo train undersampling a segment of k-space to be scanned for an acquisition of image data, and to acquire said image data from said second echo train after said second excitation pulse;
said control unit being configured to store the acquired image data in an incomplete image data set; and
an image computer having access to said memory and configured to generate an image data set by substituting data that are missing in the incomplete image data set due to the undersampling, using a selected parallel acquisition reconstruction technique using said coil calibration data; and
said control unit being configured to operate said data acquisition unit to generate said first echo train and said second echo train with an identical sequence technique such that each of said first and second echo trains to be comprised of a series of echoes, with a time interval between successive echoes of the first echo train being shorter than a time interval between successive echoes of the second echo train.

16. A non-transitory computer-readable medium encoded with programming instructions, said medium being loaded into a computer system of a magnetic resonance apparatus, comprising a magnetic resonance data acquisition unit, and said programming instructions causing said computer system to:
operate said data acquisition unit to generate a first echo train after a first excitation pulse, said first echo train sufficiently densely scanning a segment of k-space to be scanned for an acquisition of coil calibration data, and to acquire said coil calibration data from said first echo train after said first excitation pulse;
electronically store the acquired coil calibration data in a coil calibration data set;
operate the data acquisition unit to generate a second echo train after a second excitation pulse, said second echo train undersampling a segment of k-space to be scanned for an acquisition of image data, and to acquire said image data from said second echo train after said second excitation pulse;
electronically store the acquired image data in an incomplete image data set;
generate an image data set by substituting data that are missing in the incomplete image data set due to the undersampling, using a selected parallel acquisition reconstruction technique using said coil calibration data; and
operate the data acquisition unit to generate said first echo train and said second echo train with an identical sequence technique such that each of said first and second echo trains to be comprised of a series of echoes, with a time interval between successive echoes of the first echo train being shorter than a time interval between successive echoes of the second echo train.

* * * * *